(12) United States Patent
Makriyannis et al.

(10) Patent No.: US 7,119,108 B1
(45) Date of Patent: Oct. 10, 2006

(54) PYRAZOLE DERIVATIVES AS CANNABINOID RECEPTOR ANTAGONISTS

(75) Inventors: Alexandros Makriyannis, Watertown, MA (US); Qian Liu, Storrs, CT (US)

(73) Assignee: University of Connecticut, Farmington, CT (US)

( * ) Notice: Subject to any disclaimer, the term of this patent is extended or adjusted under 35 U.S.C. 154(b) by 325 days.

(21) Appl. No.: 10/110,865

(22) PCT Filed: Oct. 18, 2000

(86) PCT No.: PCT/US00/41239

§ 371 (c)(1),
(2), (4) Date: Oct. 21, 2002

(87) PCT Pub. No.: WO01/29007

PCT Pub. Date: Apr. 26, 2001

Related U.S. Application Data

(60) Provisional application No. 60/159,993, filed on Oct. 18, 1999.

(51) Int. Cl.
*A61K 31/445* (2006.01)
*C07D 401/00* (2006.01)

(52) U.S. Cl. ........................ 514/341; 546/211
(58) Field of Classification Search ............... 546/211
See application file for complete search history.

(56) References Cited

U.S. PATENT DOCUMENTS

| | | |
|---|---|---|
| 3,041,343 A | 6/1962 | Jucker et al. |
| 3,465,024 A | 9/1969 | Brownstein et al. |
| 3,573,327 A | 3/1971 | Miyano |
| 3,577,458 A | 5/1971 | Brownstein et al. |
| 3,656,906 A | 4/1972 | Bullock |
| 3,838,131 A | 9/1974 | Gauthier et al. |
| 3,886,184 A | 5/1975 | Matsumoto et al. |
| 3,897,306 A | 7/1975 | Vidic |
| 3,915,996 A | 10/1975 | Wright |
| 3,928,598 A | 12/1975 | Archer |
| 3,944,673 A | 3/1976 | Archer |
| 3,946,029 A | 3/1976 | Descamps et al. |
| 3,953,603 A | 4/1976 | Archer |
| 4,036,857 A | 7/1977 | Razdan et al. |
| 4,054,582 A | 10/1977 | Blanchard et al. |
| 4,087,545 A | 5/1978 | Archer et al. |
| 4,087,546 A | 5/1978 | Archer et al. |
| 4,087,547 A | 5/1978 | Archer et al. |
| 4,088,777 A | 5/1978 | Archer et al. |
| 4,102,902 A | 7/1978 | Archer et al. |
| 4,152,450 A | 5/1979 | Day et al. |
| 4,171,315 A | 10/1979 | Ryan et al. |
| 4,176,233 A | 11/1979 | Archer et al. |
| 4,179,517 A | 12/1979 | Mechoulam |
| 4,188,495 A | 2/1980 | Althuis et al. |
| 4,208,351 A | 6/1980 | Archer et al. |
| 4,278,603 A | 7/1981 | Thakkar et al. |
| 4,282,248 A | 8/1981 | Mechoulam et al. |
| 4,382,943 A | 5/1983 | Winter et al. |
| 4,395,560 A | 7/1983 | Ryan |
| 4,497,827 A | 2/1985 | Nelson |
| 4,550,214 A | 10/1985 | Mehta |
| 4,758,597 A | 7/1988 | Martin et al. |
| 4,812,457 A | 3/1989 | Narumiya |
| 4,876,276 A | 10/1989 | Mechoulam |

(Continued)

FOREIGN PATENT DOCUMENTS

| | | |
|---|---|---|
| EP | 0276732 | 8/1988 |
| EP | 0444451 | 9/1991 |
| EP | 0471609 | 6/1993 |
| EP | 0576357 | 12/1993 |
| EP | 0737671 | 10/1996 |
| EP | 0860168 | 9/2001 |
| FR | 2240003 | 5/1975 |
| FR | 2735774 | 1/2000 |
| GB | 2027021 A | 2/1980 |
| IL | 1995-113228 | 9/1999 |
| JP | 57098228 | 6/1982 |
| JP | 2304080 | 12/1990 |
| WO | WO 94/12466 | 6/1994 |
| WO | WO 97/00860 | 1/1997 |
| WO | WO 97/21682 | 6/1997 |
| WO | WO 99/57106 | 11/1999 |
| WO | WO 99/57107 | 11/1999 |
| WO | WO 99/64389 | 12/1999 |
| WO | WO 00/32200 | 6/2000 |
| WO | WO 01/28329 | 4/2001 |

(Continued)

OTHER PUBLICATIONS

European Search Report; European Patent Application No. EP 00 98 2694; (Four (4) Pages.

Azido–and Isothiocyanato–Substituted Aryl Pyrazoles Bind Covalently to the $CB_1$ Cannabinoid Receptor and Impair Signal Transduction; Allyn C. Howlett et al; pp. 2174–2181.

U.S. Appl. No. 09/600,786, filed Nov. 24, 1999, Makriyannis et al.

U.S. Appl. No. 09/701,989, filed Jun. 9, 1999, Makriyannis et al.

U.S. Appl. No. 10/110,830, filed Oct. 18, 2000, Makriyannis et al.

(Continued)

*Primary Examiner*—Kamal Saeed
(74) *Attorney, Agent, or Firm*—Alix, Yale & Ristas, LLP

(57) ABSTRACT

Novel cannabimimetic pyrazole derivatives are presented which have preferentially high affinities for both of the cannabinoid CB1 or CB2 receptor sites. The improved receptor affinity makes these analogs useful as experimental tools for cannabinoid receptor studies as well as clinically useful agents in individuals and animals for treatment of memory deficits associated with aging or neurological diseases, as anti-obesity agents, as medications for schizophrenia and treatment of septic shock syndrome.

6 Claims, No Drawings

U.S. PATENT DOCUMENTS

| | | | |
|---|---|---|---|
| 4,885,295 | A | 12/1989 | Bell et al. |
| 5,053,548 | A | 10/1991 | Tanaka et al. |
| 5,068,234 | A | 11/1991 | D'Ambra et al. |
| 5,147,876 | A | 9/1992 | Mizuchi et al. |
| 5,223,510 | A | 6/1993 | Gubin et al. |
| 5,284,867 | A | 2/1994 | Kloog |
| 5,324,737 | A | 6/1994 | D'Ambra et al. |
| 5,434,295 | A | 7/1995 | Mechoulam et al. |
| 5,440,052 | A | 8/1995 | Makriyannis et al. |
| 5,462,960 | A | 10/1995 | Barth et al. |
| 5,489,580 | A | 2/1996 | Makriyannis et al. |
| 5,521,215 | A | 5/1996 | Mechoulam |
| 5,532,237 | A | 7/1996 | Gallant et al. |
| 5,538,993 | A | 7/1996 | Mechoulam |
| 5,576,436 | A | 11/1996 | McCabe et al. |
| 5,605,906 | A | 2/1997 | Lau |
| 5,607,933 | A | 3/1997 | D'Ambra et al. |
| 5,618,955 | A | 4/1997 | Mechoulam et al. |
| 5,624,941 | A | 4/1997 | Barth et al. |
| 5,631,297 | A | 5/1997 | Pate et al. |
| 5,635,530 | A | 6/1997 | Mechoulam |
| 5,688,825 | A | 11/1997 | Makriyannis et al. |
| 5,744,459 | A | 4/1998 | Makriyannis et al. |
| 5,747,524 | A | 5/1998 | Cullinan et al. |
| 5,804,601 | A | 9/1998 | Kato et al. |
| 5,817,651 | A | 10/1998 | D'Ambra et al. |
| 5,872,148 | A | 2/1999 | Makriyannis et al. |
| 5,874,459 | A | 2/1999 | Makriyannis et al. |
| 5,925,628 | A | 7/1999 | Lee et al. |
| 5,925,768 | A | 7/1999 | Barth et al. |
| 5,932,610 | A | 8/1999 | Shohami et al. |
| 5,939,429 | A | 8/1999 | Kunos et al. |
| 5,948,777 | A | 9/1999 | Bender et al. |
| 6,013,648 | A | 1/2000 | Rinaldi et al. |
| 6,028,084 | A | 2/2000 | Barth et al. |
| 6,096,740 | A | 8/2000 | Mechoulam |
| 6,166,066 | A | 12/2000 | Makriyannis et al. |
| 6,284,788 | B1 | 9/2001 | Mittendorf et al. |
| 6,391,909 | B1 | 5/2002 | Makriyannis et al. |
| 6,579,900 | B1 | 6/2003 | Makriyannis et al. |
| 6,610,737 | B1 | 8/2003 | Garzon et al. |
| 2002/0119972 | A1 | 8/2002 | Leftheris et al. |
| 2002/0173528 | A1 | 11/2002 | Fride et al. |
| 2003/0120094 | A1 | 6/2003 | Makriyannis et al. |
| 2003/0149082 | A1 | 8/2003 | Makriyannis et al. |
| 2004/0077649 | A1 | 4/2004 | Makriyannis et al. |
| 2004/0077851 | A1 | 4/2004 | Makriyannis et al. |
| 2004/0087590 | A1 | 5/2004 | Makriyannis et al. |

FOREIGN PATENT DOCUMENTS

| | | |
|---|---|---|
| WO | WO 01/28497 | 4/2001 |
| WO | WO 01/28498 | 4/2001 |
| WO | WO 01/28557 | 4/2001 |
| WO | WO 01/32169 | 5/2001 |
| WO | WO 01/58869 | 8/2001 |
| WO | WO 02/058636 | 8/2002 |
| WO | WO 02/060447 | 8/2002 |
| WO | WO 03/005960 | 1/2003 |
| WO | WO 03/020217 | 3/2003 |
| WO | WO 03/035005 | 5/2003 |
| WO | WO 03/063758 | 8/2003 |
| WO | WO 03/064359 | 8/2003 |

OTHER PUBLICATIONS

U.S. Appl. No. 10/110,812, filed Oct. 18, 2000, Makriyannis et al.

U.S. Appl. No. 10/110,862, filed Oct. 18, 2000, Makriyannis et al.

U.S. Appl. No. 10/111,059, filed Oct. 18, 2000, Makriyannis et al.

U.S. Appl. No. 10/483,482, filed Jul. 11, 2002, Makriyannis et al.

U.S. Appl. No. 10/493,093, filed Oct. 28, 2002, Makriyannis et al.

U.S. Appl. No. 10/,647,544, filed Aug. 25, 2003, Makriyannis et al.

U.S. Appl. No. 10/790,498, filed Mar. 1, 2004, Makriyannis et al.

Abadji V., Lin S., Taha G., Griffin G., Stevenson L.A., Pertwee R.G., Makriyannis A.; "(R)–Methanadamide: a chiral novel anandamide possessing higher potency and metabolic stability"; J. Med. Chem.; 37(12); 1889–1893; 1994; CODEN; JMCMAR; ISSN: 0022–2623; XP002040932.

Alo, B.I.; Kandil, A.; Patil, P. A.; Sharp, M. J; Siddiqui, M. A.; and Snieckus, V. Sequential Directed Ortho Metalation– Boronic Acid Cross–Coupling Reactions. A general Regiospecific Route to Oxygenated Dibenzo[b,d] pyran–6–ones Related to Ellagic Acid, J. Org. Chem. 1991, 56, 3763–3768.

*** Archer et al; "cannabinoids, synthesis approaches to 9–ketocannabinoids."; J. Org. Chem.; vol. 42; No. 13; 2277–2284; (1977).

Arnone M., Maruani J., Chaperon P, et al, Selective inhibition of sucrose and ethanol intake by SR141716, an antagonist of central cannabinoid (CB1) receptors, Psychopharmacal, (1997) 132, 104–106. (abstract only).

Barnett–Norris et al; "Exploration of biologically relevant conformations of anandamide, . . . "; J. Med. Chem.; vol. 41; 4861–4872; 1998.

Beak, P.; and Brown, R A., The Tertiary Amide as an Effective Director of Ortho Lithiation, J. Org. Chem. 1982, 47, 34–36.

Belgaonkar et al; "synthesius of isocoumarins"; Indian J. Chem; vol. 13; No. 4; 336–338; 1975 (abstract only).

Beltramo M., Stella N., Calignano A., Lin S. Y., Makriyannis A., Piomelli D; "Functional Role Of High–Affinity Anandamide Transport, as Revealed By Selective Inhibition"; Science; vol. 277; 1094–1097; 1997.

Beltramo M., Stella N., Calignano A., Lin S. Y., Makriyannis A., Piomelli D; "Identification and Functional Role of High Affinity Anandamide Transport"; The Neurosciences Institute (1 page).

Berdyshev EV, Cannabinoid receptors and the regulation of immune response. Chem Phys Lipids. Nov. 2000; 108(1–2):169–90.

Berglund et al; "Structural requirements for arachidonylethanolamide interaction with CB1 and CB2 cannabinoid receptors: . . . "; Prostanglandins, leukotrienes ands essential fatty acids; 59(2); 111–118; (1998). (abstract only).

Bodnar, V.N., Lozinskii, M.O., Pel'kis, P.S.; "Synthesis of 2,5–disubstituted 1,3,4–oxadiazoles and 1,4–dihydro–1,2,4, 5–tetrazines"; Ukrainskii Khimicheskii Zhurnal (Russian Edition); 48(12); 1308–1311; 1982 (abstract only).

Bracey, M et al, Structural Adaptations in a Membrane Enzyme That Terminates Endocannabinoid Signaling. Science 2002; 298(5599): 1793–1796.

Brenneisen R, Pgli A, Elsohly MA, Henn V. Spiess Y: The effect of orally and rectally administered 9—tetrahydrocannabinol on spasticity, a pilot study with 2 patients. Int. J. Clin Pharmacol Ther. (1996) 34:446–452. (abstract only).

\*\*\* Brotchie JM: *Adjuncts to dopamine replacement a pragmatic approach to reducing the problem of dyskinesia in Parkinson's disease. Mov. Disord.* (1998) 13:871–876.

Brown et al; "Synthesis and hydroboration of(−)–2–phenylapopinene, Comparison of mono(2–phenylapoisopinocampheyl)borane with its 2–methyl and 2–ethyl analogues for the chiral hydroboration of representative alkenes"; J. Org. Chem.; 55(4); 1217–1223; (1990).

Buckley NE, McCoy KI, Mpzey E et al, "Immunomodulation by cannabinoids is absent in mice deficient for the cannabinoid CB2 receptor"; Eur. J Pharmacol (2000) 396:141–149.

Burstein et al; "detection of cannabinoid receptors . . . "; Biochem. Biophys. Res. Commun.; vol. 176(1); 492–497; 1991 (abstract only).

Busch–Peterson et al; "Unsaturated side chain beta–11–hydroxyhexahydrocannabinol analogs"; J. Med. Chem.; 39; 3790–3796; (1996).

Calignano A, La Rana G. Diuffrida A, Piomelli D; "Control of pain initiation by endogenous cannabinoids"; Nature (1998) 394:277–291. (abstract only).

Calignano A., La Rana G., Beltramo, M., Makriyannis A., Piomelli D; "Potentiation of Anandamide Hypotension by the Transport Zinhibitor, AM404"; Eur. J. Pharmocol.; 1997; 337 R1–R2.

Calignano A., La Rana G., Makriyannis A., Lin. S., Beltramo M., Piomelli D; "Inhibition of Intestinal Motility by Anandamide, an Endogenous Cannabinoid"; Eur. J. Pharmacol.; 1997; 340 R7–R8.

Campbell FA et al; "Are cannabinoids an effective and safe treatment option in the management of pain? A qualitative systematic review"; BMJ. Jul. 7, 2001;323(7303):13–6.

Charalambous A. et al; "5'–azido 8–THC: A Novel Photoaffinity Label for the Cannabinoid Receptor"; J. Med. Chem., 35, 3076–3079 (1992).

Charalambous A. et al; "Pharmacological evaluation of halogenated . . . "; Pharmacol. Biochem. Behav.; vol. 40; No. 3; 509–512; 1991.

Cheng et al; "Relationship Between the Inhibition Constant (Ki) and the concentration of Inhibitor which causes 50% Inhibition (IC50) of an Enzymatic Reaction"; Biochem. Pharmacol., 22, 3099–3102, (1973) (abstract only).

Cherest M., Luscindi X.; "The action of acetyl chloride and of acetic anhydride on the lithium nitronate salt of 2–phenylnitroethane . . . "; Tetrahedron; 42(14); 3825–3840; 1986; in French with English abstract.

Cherest M., Lusinchi X.; "A novel electrophilic N–amidation via electron deficient complexes: action of ferric chloride on N–acetyloxyamides"; Tetrahedron Letters; 30(6); 715–718; 1989.

Colombo G, Agabio R, Diaz G. et al; "Appetite suppression and weight loss after the cannabinoid antagonist SR141716"; Life Sci. (1998) 63–PL13–PL117. (abstract only).

\*\*\* Compton D.R. et al; *J. Pharmacol. Exp. Ther.*; 260; 201–209; 1992.

Compton et al; "Synthesis and pharmacological evaluation of ether and related analogues of delta8–. delta9– and delta9,11–tetrahydrocannabinol"; J. Med. Chem; vol. 34; No. 11; 3310–3316; 1991.

Consroe P, Musty R, Rein J, Tillery W, Pertwee R; "The perceived effects of smoked cannabis on patents with multiple sclerosis"; Eur. Neurol. (1997) 38–44–48. (abstract only).

Coxon et al; "Derivatives of nopinone"; Aust. J. Chem.; 23; 1069–1071; (1970) (abstract only).

Crawley et al; "Anandamide, an endogenous ligand of the cannabinoid receptor, induces hypomotility and hypothermia in vivo in rodents"; Pharmacology Biochemistry and Behavior; vol. 46; 967–972; 1993.

D'Ambra et al; "C–attached aminoalkylindoles: potent cannabinoid mimetics"; Bioorg. & Med. Chem. Lett., 1996, 6(1), 17–22.

\*\*\* D'Amour F.E., Smith D.L.; *J. Pharmacol. Exp. Ther.*; 72; 74–79; 1941.

Demuynck L. et al; "Rearrangement of Indolo[2,3–a]quinolizidines to derivatives with E–azaaspidospermane skeleton"; Tetrahedron Letters; 30(6) 710–722; 1989; in French with English abstract.

DePetrocellis L, Melck D, Palmisano A. et al; "The endogenous cannabinoid anandamide inhibits human breast cancer cell proliferation"; Proc. Natl. Acad. Sci. USA (Jul. 1998) 95:8375–8380.

Desarnaud F., Cadas H., Piomelli D.; "Anandamide amidohydrolase activity in rat brain microsomes"; J. Biol. Chem.; 270; 6030–6035; (1995).

Deutsch D.G. et al; "Fatty acid sulfonyl fluorides inhibit anandamide metabolism and bind to cannabinoid receptor"; Biochem. Biophys. Res. Commun. 231(1); 217–221; 1997; CODEN: BBRCA9; ISSN:0006–291X; XP002040933.

Deutsch D.G., Chin S.A.; "Enzymatic synthesis and degradation of anandamide, a cannabinoid receptor agonist"; Biochemical Pharmacology; 46(5); 791–796; 1993.

Devane, W.A. et al; "Determination and Characterization of a Cannabinoid Receptor in a Rat Brain"; Mol. Pharmacol., 34, 605–613 (1988). (abstract only).

Di Marzo, V., Melck, D., Bisogno, T., DePetrocellis, L.; "Endocannabinoids: endogenous cannabinoid receptor ligands with neuromodulatory action"; Trends Neurosci. (1998) 21:521–528.

\*\*\* Dodd, P.R. et al, *A Rapid Method for Preparing Synaptosomes: Comparison with Alternative Procedures, Brain Res.*, 226, 107–118 (1981).

Dominiami et al; "Synthesis 5–(tert–Alkyl)resorcinols"; J. Org. Chem. 42(2); 344–346; (1977).

Drake et al, "classical/nonclassical hybrid cannabinoids"; J. Med. Chem.; vol. 41(19); 3596–3608 (1998).

Edery et al; "Activity of novel aminocannabinoids in baboons"; J. Med. Chem., 27; 1370–1373 (1984).

Eissenstat et al; "Aminoalkylindoles: structure–activity relationships of novel cannabinoid mimetics"; J. Med. Chem. 1995, vol. 38, No. 16, pp. 3094–3105; XP 000651090.

Fahrenholtz, K. E., Lurie, M. and Kierstead, AR. W.; "The Total Synthesis of dl–$\Delta$9–Tetrahydrocannabinol and Four of Its Isomers"; J. Amer. Chem. Soc. 1967, 89(23), 5934–5941.

Fahrenholtz; "The synthesis of 2 metabolites of (−)–delta eight–tetrahydrocannabinol"; J. Org. Chem.; vol. 37(13); 1972; XP002111824.

Fisera, L., Kovac, J., Lesco, J., Smahovsky, V.; "Furan derivatives. Part CLVI. 1,3–dipolar cycloadditions of heterocycles. V. Reaction of C–acetyl–N–phenylnitrilimine with furan derivatives"; Chemicke Zvesti; 35(1); 93–104 1981 (abstract only).

Fride, E. & Mechoulam, R.; "Pharmacological activity of the cannabinoid receptor agonist, anandamide, a brain constituent"; European Journal of Pharmacology, vol. 231; 313–314; 1993.

Galiegue S et al. ; "Expression of central and peripheral cannabinoid receptors in human immune tissues and leukocyte subpopulations"; Eur J Biochem.; Aug. 15, 1995;232(1):54–61. (abstract only).

Gareau, Y.; Dufresne, C.; Gallant, M.; Rochette, C.; Sawyer, N.; Slipetz, D. M.; Tremblay, N.; Weech, P. K.; Metters, K. M.; Labelle, M.; "Structure activity relationships of tetrahydrocanabinol analogs on human cannabinoid receptors"; Bioorg. Med. Chem. Lett. 1996, 6(2), 189–194.

Gold et al; "A comparison of the discriminative stimulus properties of delta9–tetrahydrocannabinol and CP 55,940 in rats and rhesus monkeys"; J. Pharmacol. Exp. Ther.; vol. 262(2); 479–486; 1992.

*** Green K. *Marijuana smoking* vs. *cannabinoids for glaucoma therapy. Arch. Ophibalmol.* (1998) feb 433–1437.

Hampson, A.J., Grimaldi M. Axpirod J. Wink D; "Cannabidiol and (–) 9 tetrahydrocannabinol are neuroprotective antioxidants"; Proc. Natl Acad Sci. USA (Jul. 1998) 95; 8268–8273.

Hargreaves, K. et al; "A new sensitive method for measuring thermal nociception in cutaneous hyperalgesia"; Pain; 32; 77–88; (1988) (abstract only).

*** Hemming M, Yellowlees PM, "*Effective treatment of Tourette's syndrome with marijuana*"; *J. Psychopharmacol*, (1993) 7:389–391.

Herzberg U, Eliav E, Bennett GJ, Kopin IJ; "The analgesic effects of R(+) WIN 55,212–2 mesylate, a high affinity cannabinoid agonist in a rat model of neuropathic pain"; Neurosci. Letts. (1997) 221; 157–160.

Hillard C. J., Edgemond, W. S., Jarrahian W., Campbell, W. B; "Accumulation of N–Arachidonoylethanolamine (Anandamide) into Cerebellar Granule Cells Occurs via Facilitated Diffusion"; Journal of Neurochemistry; 69; 631–638 (1997).

Horrevoets A.J.G et al; "Inactivation of *escherichia coli* outer membrane phospholipase A by the affinity label hexadecanesulfonyl fluoride"; Eur. J. Biochem.; 198; 247–253; 1991.

Horrevoets A.J.G et al; "Inactivation of reconstiuted *escherichia coli* outer membrane phospholipase A by membrane–perturbing peptides results in an increased reactivity towards the affinity label hexadecanesulfonyl fluoride"; Eur. J. Biochem.; 198; 255–261; 1991.

Howlett et al; "Stereochemical effects of 11–OH–delta 8 tetrahydrocannabinol–dimethylheptyl to inhibit adenylate cyclase and bind to the cannabinoid receptor"; Neuropharmacology; vol. 29(2); 161–165; 1990.

Huffman et al; "3–(1',1'–dimethylbutyl)—deoxy–delta 8THC and related compounds: synthesis selective ligands for the CB2 receptor"; Bioorganic and Medicinal Chemistry; vol. 7; 2905–2914; (1999).

Huffman et al; "Stereoselective synthesis of the epimeric delta 7–tetrahydocannabinols"; tetrahedron; vol. 51(4); 1017–1032; (1995).

Huffman et al; "Synthesis of 5',11 dihydroxy delta 8 tetrahydrocannabinol"; Tetrahedron, vol. 53(39), pp. 13295–13306 (1997).

Huffman et al; "Synthesis of a tetracyclic, conformationally constrained analogue of delta8–THC"; Bioorganic & Medicinal Chemistry; vol. 6(12); 2281–2288; 1998; XP002123230.

Huffman et al; "Synthesis of both enantiomers of Nabilone from a common intermediate. Enantiodivergent synthesis of cannabinoids"; J. Org. Chem.; 1991, 56, 2081–2086.

*** Joy JE, Wagtson SJ, Benson JA; "Marijuana and Medicine Assessing the Science Base"; *National Academy Press*, Washington, DC, USA (1999).

Kaminski NE; "Regulation of the cAMP cascade, gene expression and immune function by cannabinoid receptors"; J Neuroimmunol. Mar. 15, 1998;83(1–2):124–32.

Kawase M. et al; "Electrophilic aromatic substitution with N–methoxy–N–acylnitrenium ions generated from N–chloro–N–methoxyamides: synthesis of nitrogen heterocyclic compounds bearing a N–methoxyamide group"; J. Org. Chem.; 54; 3394–3403; 1989.

Khanolkar A., Abadji V., Lin S., Hill W., Taha G., Abouzid K., Meng Z., Fan P., Makriyannis A.; "Head group analogues of arachidonylethanolamide, the endogenous cannabinoid ligand"; J. Med. Chem.; vol. 39(22); 4515–4519; (1996).

Khanolkar et al; "Molecular probes for the cannabinoid receptors"; Chemistry and Physics of Lipids; 108; 37–52; (2000).

Klein T.W. et al, "The cannabinoid system and cytokine network"; Proc Soc Exp Biol Med. Oct. 2000; 225(1):1–8; (abstract only).

Klein TW et al, "Cannabinoid receptors and immunity"; Immunol Today; Aug. 1998; 19(8):373–81.

Koutek B. et al; "Inhibitors of arachidonyl ethanolamide hydrolysis"; J. Biol. Chem.; 269(37); 22937–40; 1994; CODEN: JBCHA3; ISSN: 0021–9258; XP002040931.

Kumar RN, et al; "Pharmacological actions and therapeutic uses of cannabis and cannabinoids"; Anesthesia, 2001, 56: 1059–1068 (abstract only).

*1* Lan, R et al; "Structure activity relationships of pyrazole derivatives as cannabinoid receptor antagonists"; J. Med. Chem.; vol. 42(4); 769–776; (1999).

Lavalle et al; "Efficient conversion of (1R, 5R)–(+)–alpha–pinene to (1S, 5R)–(–)–nopinene"; J. Org. Chem.; vol. 51(8); 1362–1365; (1986).

Lin S., Khanolkar A., Fan P., Goutopolous A., Qin C., Papahadjis D., Makriyannis A.; "Novel Analogues of arachidonylethanolamide (anandamide): affinities for the CB1 and CB2 Cannabinoid Receptors and Metabolic Stability"; J. Med. Chem.; vol. 41; 5353; 1998.

Loev, B., Bender, P. E., Dowalo, F., Macko, E., and Fowler, P.; "Cannabinoids. Structure–Activity Studies Related to 1,2–Dimethylheptyl Derivatives"; J. Med. Chem.; vol. 16(11); 1200–1206; 1973.

Lozinskii, M.O., Bodnar, V.N., Konovalikhin, S.V., D'yachenko, O.A., Atovmyan, L.O.; "Unusual transformations of arylhydrazonoyl chlorides of oxalic acid ethyl ester"; Izvestiya Akademii Nauk SSSr, Seriya Khimicheskaya; 11; 2635–2637; 1990 (abstract only).

Ludt, R.E. et al; "A comparison of the synthetic utility of n–butyllithium and lithium diisopropylamide in the metalations of N,N–dialkyltouamides"; J. Org. Chem.; 38(9); 1668–1674 (1973).

*** Maccarron M., *Endocannabinoids and their actions. Vitamins and Hormones* 2002;65:225–255.

Mackie K., Devane W.A., Hille B.; "Anandamide, an endogenous cannabinoid, inhibits calcium currents as a partial agonist in N18 neuroblastoma cells"; Mol. Pharmacol; 44; 498–0503 (1993).

*** Markwell et al; *Anal. Biochem.*; 87:206 (1978).

Martin et al; "Behavioral, biochemical, and molecular modeling evaluations of cannabinoid analogs"; Pharmacol. Biochem. Behav.; vol. 40(3); 471–478; 1991.

Martyn CN. Illis LS, Thom J.; "Nabilone in the treatment of multiple sclerosis"; Lancet (1995) vol. 345; pp. 579.

Matsumoto et al; "Cannabinoids 1.1–amino–and 1 mercapto–7,8,9,10–tetrahydro–6h–dibenzo[b,d]pyrans"; J. of Med. Chem.; vol. 20(1); 17–24; 1977; XP00211825.

*** Maurer M, Henn V, Dittrich A, Hofmann A. *Delta–9–tetrahydrocannabinol shows antispastic and analgesic effects in a single case double–blind trial. Eur. Arch. Psychiat. Clin. Neurosci.* (1990), Z40:1–4.

Mavromoustakos, T. et al; "Studies on the thermotropic effects of cannabinoids on phosphatidylcholine bilayers using differential scanning calorimetry and small angle X–ray diffraction"; Biochimica et Biophysica Acta; vol. 1281(2); 1996; XP002111823.

Mechoulam et al; "Stereochemical Requirements for cannabinoid activity"; J. Med. Chem.; 23(10); 1068–1072; (1980).

Mechoulam et al; "Synthesis of the individual, pharmacologically distinct, enantiomers of a tetrahydrocannabinol derivative"; Tetrahedron Asymmetry; 1: 311–314; (1990) (abstract only).

*** Mechoulam et al; *Tetrahedron Asymmetry*; 1: 315–318; (1990).

*** Mechoulam, *"Cannabinoids as therapeutic agents"; CRC press*, 1986.

Meltzer et al; "An improved synthesis of cannabinol and cannabiorcol"; Synthesis; 1981:985 (1981).

*** Melvin et al; *drug design and discovery*; 13; 155–166 (1995).

Melvin et al; "Structure–activity relationships for cannabinoid receptor–binding and analgesic activity: studies of bicyclic cannabinoid analogs"; Mol. Pharmacol.; 44(5); 1008–1015 (1993).

Merck Index; 11th edition; "Tetrahydrocannabinols" compound No. 9142; 1989.

*** Morgan Dr: *Therapeutic Uses of Cannabis. Harwood Academic Publishers*, Amsterdam. (1997).

*** Morris, S,; Mechoulam, R.; and Irene, Y., *Halogenation of phenols and Phenyl ethers with Potassium Halides in the Presence of 18–Crown–6 on Oxidation with m–Chloroperbenzoic Acid, J. Chem. Soc., Perkin Trans.* 1 1987, 1423–1427.

*** Muller–Vahl KB, Kolbe H, Schneider U, Emrich, HM *Cannabis in movement disorders. Porsch. Kompicmentarmed* (1999) 6 (suppl. 3) 23–27.

*** Muller–Vahl KB, Schneider U, Kolbe H, Emrich, HM. *Treatment of Tourette's syndrome with delta–9–tetrahydrocannabinol. Am. J. Psychiat.* (1999) 156–195.

*** Nahas G, *Marijuana and Medicine*; 1999, Human Press Inc., Totowa, NJ.

Neunhoeffer O., Gottschlich R.; "Acylating activity of O–acylated hydroxylamine derivatives"; Justus Liebigs Ann. Chem.; 736; 100–109; 1970; in German with English abstract.

Novak, J et al; Cannabis, part 27, synthesis of 8–, 10– and 11–oxygenated cannabinoids; J. Chem. Soc. Perkin Trans.; 2867–2871; (1983) (abstract only).

Nye et al; "High affinity cannabinoid binding sites in brain membranes labelled with [H]–5'–trimethylammonium delta8–tetrahydrocannabinol"; J. Pharmacol. Exp. Ther.; vol. 234(3); 784–791; 1985.

*** Palmer et al; *current pharmaceutical design*; 6; 1381–1397; (2000).

Papahatjis et al; "A new ring–forming methodology for the synthesis of conformationally constrained bioactive molecules"; Chemistry Letters, 192; (2001).

Papahatjis et al; "Pharmacophoric requirements for cannabinoid side chains: multiple bond and $C1^1$ –substituted delta8–tetrahydrocannabinols"; J. Med. Chem.; 41(7); 1195–1200; (1998).

Pertwee et al; "AM630, a competitive cannabinoid receptor agonist"; Life Sci. 1995, 56(23/24), 1949–1955; XP 000653566.

Pertwee et al; "Pharmacological characterization of three novel cannabinoid receptor agonists in the mouse isolated vas deferens"; Eur. J. Pharmacol. 1995, 284, 241–247; XP–001041044.

*** Pertwee et al; *Br. J. Pharmacol.*; 105; 980 1992.

Pertwee; Pharmacology pf cannabinoid CB1 and CB2 receptors; Pharmacol. Ther., vol. 74(2); pp. 129–180; (1997); XP002226467.

Petrov, M.L., Terent'eva, N.A., Potekhin, K.A., Struchkov, Yu. T.; ".alpha.,.beta.–unsaturated thiolates and their analogs in cycloaddition reactions. XVIII. Reaction of (2–phenylethynyl)tellurolates with C–ethoxycarbonyl–N–Phenylnitrilimine"; Zhurnal Organicheskoi Khimii; 29(7); 1372–1378; (1993) (abstract only).

*** Pinnegan–Ling D, Musty R.; *Marinol and phantom limb pain: a case study. Proc Inv. Cannabinoid Rea. Sec.* (1994):53.

Piomelli D., Beltramo M., Glasnapp S., Lin S.Y., Goutopoulos A., Xiw X–Q., Makriyannis A.; "Structural determinants for recognition and translocation by the anandamide transporter"; Proc. Natl. Acad. Sci. USA; 96; 5802–5807; (1999).

Pitt et al; "The synthesis of Deuterium, carbon–14 and carrier free tritium labelled cannabinoids"; Journal of Labellled Compounds; vol. 11(4); 551–575; 1975; XP002123229.

***Porreca F., Mosberg H.I., Hurst R., Hruby V.J., Burks T.F.; "Roles of mu, delta and kappa opiod receptors in spinal supraspinal mediation of gastrointestinal transit effects and hot–plate analgesia in the mouse"; J. Pharmacol. Exp. Ther.; 230, 341–348; (1994).

Razdan et al; "Drugs derived from cannabinoids. 6. .Synthesis of cyclic analogues of dimethylheptylpyran"; J. Med. Chem.; vol. 19(5); 719–721; 1976 (abstract only).

Reggio et al; "Characterization of a region of steric interference at the cannabinoid receptor using the active analog approach"; J. Med. Chem. United States; vol. 36(12); 1761–1771; 1993.

Rhee, M. H.; Vogel, Z.; Barg, J.; Bayewitch, M.; Levy, R.; Hanus, L.; Breuer, A.; and Mechoulam, R.; "Cannabinol Derivatives: Binding to Cannabinoid Receptors and Inhibition of Adenylcyclase"; J. Med. Chem. 1997, 40(20); 3228–3233.

*** Rice AS. *Cannabinoids and pain. Curr Opin Investig Drugs.* Mar. 2001;2(3):399–414.

Richardson JD, Aanonsen I, Hargreaves KM; "Antihyperalgesic effects of a spinal cannabinoids"; Eur. J. Pharmacol. (1998) 346:145–153.

Richardson JD, Kilo S. Hargreaves KM; "Cannabinoids reduce dryperalgesia and inflammation via interaction with peripheral CB1 receptors"; Pain (1998) 75:111–119.

*1* Rinaldi–Carmona et al; "Biochemical and pharmacological characterization of SR141716A, the first potent and selective brain cannabinoid receptor antagonist"; Life Sci.; vol. 56(23/24); 1941–1947 (1995).

*1* Rinaldi–Carmona et al; "SR141716A, a potent and selective antagonist of the brain cannabinoid receptor"; FEBS Lett.; 350; 240–244: (1994).

Rompp Chemie Lexikon; Falbe and Regitz; "band 1–A–C1, 8"; Aufl, Thieme Verlag; Stuttgart, S 569–570; 1989.

Santus, Maria; "Studies on thioamides and their derivatives. IX. Synthesis of the derivatives of 1,2,4,5–tetrazine"; Acta Polonae Pharmaceutica; 50(2–3); 183–188; 1993 (abstract only).

Schatz AR et al; "Cannabinoid receptors CB1 and CB2: a characterization of expression and adenylate cyclase modulation within the immune system"; Toxicol Appl Pharmacol. Feb. 1997; 142(2):278–87.

*** Schuel, H., Burkman, L.J., Picone, R.P., Bo, T., Makriyannis, A., *Cannabinoid receptors in human sperm. Mol. Biol. Cell.*, (1997) (8), 325a.

*** Serdarevich B., Caroll K.K., *"Synthesis and characterization of 1– and 2–monoglycerides of anteiso fatty acids"*; J. Lipid Res.; 7; 277–284; (1966).

Shawali, A.S., Albar, H.A.; "Kinetics and mechanism of dehydrochlorination of N–aryl–C–ethoxycarbonyl formohydrazidoyl chlorides"; Canadian Journal Of Chemistry; 64(5); 871–875; 1986 (abstract only).

*** Shen M. Thayer SA: *Cannabinoid receptor agonists protect cultured rat hippocampal neurons from excitotoxicity.* Mol. Pharmacol (1996) 54:459–462.

Shim et al; "Three–dimensional quantitative structure–activity relationship study of the cannabimimetic (aminoalkyl)indoles using comparative molecular field analysis"; J. Med. Chem.; 1998, 41(23); 4521–4532; XP–002212407.

Shim et al; "Unified pharmacophoric model for cannabinoids and aminoalkylindoles derived from molecular superimposition of CB1 cannabinoid receptor agonists CP55244 and WIN55212–2"; ACS Symposium series, 1999 719 (rational drug design), 165–184; XP–001095771.

Showalter et al; "Evaluation of binding in a transfected cell line expressing a peripheral cannabinoid receptor (CB2): identification of cannabinoid receptor subtype selective ligands"; J. Pharmacol. Exp. Ther., 1996 278(3) 989–999; XP–001097918.

*** Simiand J, Keane M, Keane PE, Soubrie P: SR 141716, *A CB1 cannabinoid receptor antagonist, selectively reduces sweet food intake in marmoset.* Behav. Pharmacol (1998) 9:179–181.

Smith P.B. et al; "The pharmacological activity of anandamide, a putative endogenous cannabinoid, in mice"; Journal of Pharmacology and Experimental Therapeutics; vol. 270(1):219–227; 1994.

*** Terranova J–P, Storme J–J Lafon N et al; "Improvement of memory in rodents by the selective CB1 cannabinoid receptor antagonist, SR 141716"; Psycho–pharmacol (1996) 126:165–172.

Tius et al; "Conformationally restricted hybrids of CP–55, 940 and HHC: Steroeselective synthesis and activity"; Tetrahedron; 50 (9); 2671–2680; (1994) (abstract only).

Twitchell, W. et al; "Cannabinoids inhibit N– and P/Q type calcium channels in cultured rat hippocampal neurons"; Journal of Neurophysiology; 78(1); 43–50; 1997 (abstract only).

*** Ueda, N., *Endocannabinoid hydrolases. Prostaglandins & Other Lipid Mediators* 2002;68–69:521–534.

*** Vogel Z., Barg., Levy R., Saya D., Heldman E., Mechoulam R.; *"Anandamide, a brain endogenous compound, interacts specifically with cannabinoid receptors and inhibits adenylate cyclase"*; J. Neurochem.; 61(1) 352–355; (1993).

*** Wagner JA, Varga K, Jarai Z, Kunos G; 'Mesenteric vasodialtion mediated by endothelia anandamide receptors'; Hypertension (1999) 33:429–434.

Watanabe, T.; Miyaura, N.; and Suzuki, A.; "Synthesis of Sterically Hindered Biaryls via the Palladium Catalyzed Cross–Coupling Reaction of Arylboronic Acids or their Esters with Haloarenes"; Synlett 1992, 207–210.

Wiley et al; "Structure activity relationships of indole and pyrrole derived cannabinoids"; J. Pharmacol. Exp. Ther. 1998, 285(3), 995–1004; XP–001097982.

Wilson et al; "9–nor–delta8–tetrahydrocannabinol, a cannabinoid of metabolic intersts"; J. Med. Chem.; 17(4); 475–476; (1974).

Wilson et al; "Analgesic properties of the tetrahydrocannabinols, their metabolites and analogs"; J. Med. Chem.; 18(7); 700–703; (1975).

Wilson et al; "9–nor–9–hydrohexahydrocannabinols. Synthesis, some behavioral and analgesic properties, and comparison with the tetrahydrocannabinols"; J. Med. Chem.; 19(9); 1165–1167; (1976).

Yamada et al; "(Aminoalkyl)indole isothiocyanates as potentiual electrophilic affinity ligands for the brain cannabinoid receptor"; J. Med. Chem. 1996, vol. 39(10), 1967–1974.

Yan, Guo et al; "Synthesis and pharmacological properties of 11–hydroxy–3–(1'–1'–dimethylheptyl)hexahydrocannabinol: a high affinity cannabinoid agonist"; J. Med. Chem.; vol. 37(16); 2619–2622; (1994).

Yan Guo et al; "(–)–11–hydroxy–7'–isothiocyanato–1'–1'dimethylheptyl–delta8–THC: a novel probe for the cannabinoid receptor in the brain"; J. Med. Chem.; 37(23); 3867–3870; (1994).

U.S. Appl. No. 09/698,071, filed Oct. 30, 2000, Fride et al.

Beltramo M., Piomelli D; "Anandamide Transport Inhibition by the Vanilloide Agonist Olvanil"; Europeean J. of Pharmacology; (1999); 364(1); 75–78 (abstract only).

Berglund et al; "Structural requirements for arachidonylethanolamide interaction with CB1 and CB2 cannabinoid receptors: . . . "; Prostanglandins, leukotrienes ands essential fatty acids; 59(2); 111–118; (1998).

*2* Brotchie JM: Adjuncts to dopamine replacement a pragmatic approach to reducing the problem of dyskinesia in Parkinson's disease. Mov. Disord. (1998)13:871–876. (abstract only).

*2* Compton D.R. et al; "Pharmacological Profile Of A Series Of Bicyclic Cannabinoid Analogs: Classification as Cannabimimetic Agents"; J. Pharmacol. Exp. Ther.; 260; 201–209; 1992. (abstract only).

Di Marzo, V., Bisogno, T., Melck, D., Ross, R., Brockie, H., Stevenson, L., Pertwee, R., DePetrocellis, L., "Interactions between synthetic vanilloids and the endogenous cannabinoid system"; FEBS Letters; (1998); 437(3); 449–454. (abstract only).

*2* Dodd, P.R. et al, A Rapid Method for Preparing Synaptosomes: Comparison with Alternative Procedures, Brain Res., 226, 107–118 (1981). (abstract only).

*2* Green K.; "*Marijuana smoking vs. cannabinoids for glaucoma therapy.*"; Arch. Ophthamol. (1998) Nov. 116(11); 1433–1437. (abstract only).

*1* Griffin, G., Wray, E. J., Tao, Q., McAllister, S. D., Rorrer, W. K., Aung, M., Martin, B. R., Abood, M. E.; "Evaluation of the cannabinoid CB2 receptor selective antagonist, SR144528: further evidence for cannabinoid CB2 receptor absence in the rat central nervous system"; European Journal of Pharmacology; (1999); vol. 377; 117–125.

Hanus et al; "Two new unsaturated fatty acid ethanolamides in brain that bind to the cannabinoid receptor"; Journal of medicinal Chemistry; 36(20); 3032–3034; 1993.

*1* Jbilo, O., Derocq, J., Segui, M., Le Fur, G., Casellas, P.; "Stimulation of peripheral cannabinoid receptor CB2 induces MCP–1 and IL–8 gene expression in human promyelocytic cell line HL60"; FEBS Letters; (1999); vol. 448; No. 21848; 273–277.

*2* Joy JE, Wagtson SJ, Benson JA; "Marijuana and Medicine Assessing the Science Base"; National Academy Press, Washington, DC, USA (1999). (abstract only).

Lang, W. et al; "Substrate Specificity and Stereoselectivity of Rat Brain Microsomal Anandamide Amidohydrolase"; J. Med. Chem.; vol. 42(5); 896–902; (1999).

*2* Maurer M, Henn V, Dittrich A, Hofmann A.; "Delta–9–tetrahydrocannabinol shows antispastic and analgesic effects in a single case double–blind trial."; Eur. Arch. Psychiat. Clin. Neurosci. (1990), 240:1–4. (abstract only).

Mechoulam et al; Structural Requirements for Binding of Anandamide Type Compounds to the Brain Cannabinoid Receptor; J. Med. Chem.; 1997; 40; 659–667.

*1* Mechoulam et al; "Towards Cannabinoid drugs—Revisited"; Progress in Medicinal Chemistry; 35; 199–243; Jul. 3, 1998.

Melck, D., Bisogno, T., DePetrocellis, L., Chuang, H., Julius, D., Bifulco, M., DiMarzo, V.; "Unsaturated Long–Chain N–Acyl–vanillyl–amides"; Biochemical and Biophysical Res. Commun.; (1999); 262(1); 275–284 (abstract only).

*2* Melvin et al; "Structure–Activity Relationships Defining the ACD–Tricyclic Cannabinoids Cannabinoid Receptor Binding and Analgesic Activity"; Drug Design and Discovery; 13(2); 155–166 (1995). (abstract only).

*1* Meschler, J. P., Kraichely, D. M., Wilken, G. H., Howlett, A. C.; "Inverse Agonist Properties of N–(Piperidin–1–yl)–5–(4–chlorophenyl)–1–(2,4–dichlorophenyl)–4–methyl–1H–pyrazole–3–carboxamide HCL (SR–141716A) and 1–(2–Chlorophenyl)–4–cyano–5–(4–methoxyphenyl)–1H–pyrazole–3–carboxylic Acid Phenylamide (CP–272871) for the CB1 Cannabinoid Receptor"; Biochemical Pharmacology; (2000); vol. 60; No. 9; 1315–1322.

*2* Muller–Vahl KB, Kolbe H, Schneider U, Emrich, HM Cannabis in movement disorders. Porsch. Kompicmentarmed (1999) 6 (suppl. 3) 23–27. (abstract only).

*2* Muller–Vahl KB, Schneider U, Kolbe H, Emrich, HM.; "Treatment of Tourette's syndrome with delta–9–tetrahydrocannabinol." Am. J. Psychiat.; (1999); 156(3); 495.

Pacheco M, et al; "Aminoalkylindoles: Actions On Specific G–Protein–Linked Receptors"; J. Pharmacol. Exp. Ther.; vol. 257, No. 1, pp. 170–183 and 172 Table (1991).

*2* Palmer et al; "Natural and Synthetic Endocannabinoids and Their Structure–Activity Relationships"; Current Pharmaceutical Design; 6; 1381–1397; (2000).

*2* Pertwee et al; "Inhibitory effects of certain enantiomeric cannabinoids in the mouse vas deferens and the myenteric plexus preparation of guinea–pig small intestine"; Br. J. Pharmacol.; 105(4); 980–984 (1992). (abstract only).

*2* Pinto et al; Cannabinoid Receptor Binding and Agonist Activity of Amides and Esters of Arachidonic Acid; Mol. Pharmacol.; 1994; 46(3); 516–522.

*2* Porreca F., Mosberg H.I., Hurst R., Hruby V.J., Burks T.F.; "Roles of mu, delta and kappa opiod receptors in spinal and supraspinal mediation of gastrointestinal transit effects and hot–plate analgesia in the mouse"; J. Pharmacol. Exp. Ther.; 230(2); 341–348; (1994). (abstract only).

*1* Quere, L., Boigegrain, R., Jeanjean, F., Gully, D., Evrard, G., Durant, F., "Structural requirements of non–peptide neurotensin receptor antagonists"; J. Chem Soc., Perkin Trans. 2, (1996); 2639–2646.

Razdan et al; "Pharmacological and Behavioral Evaluation of Alkylated Anandamide Analogs"; Life Sci.; 1995; 56(23–24); 2041–2048.

*2* Rice AS. Cannabinoids and pain. Curr Opin Investig Drugs. Mar. 2001;2(3):399–414. (abstract only).

*2* Serdarevich B., Caroll K.K., "Synthesis and characterization of 1– and 2–monoglycerides of anteiso fatty acids"; J. Lipid Res.; 7; 277–284; (1966).

*2* Shen M. Thayer SA: Cannabinoid receptor agonists protect cultured rat hippocampal neurons from excitotoxicity. Mol. Pharmacol (1996) 54:459–462.

*2* Simiand J, Keane M, Keane PE, Soubrie P: SR 141716, A CB1 cannabinoid receptor antagonist, selectively reduces sweet food intake in marmoset. Behav. Pharmacol (1998) 9:179–181. (abstract only).

*2* Terranova J–P, Storme J–J Lafon N et al; "Improvement of memory in rodents by the selective CB1 cannabinoid receptor antagonist, SR 141716"; Psycho–pharmacol (1996) 126:165–172 (abstract only).

Tetko, I. V. et al; "Volume Learning Algorithm Artificial Neural Networks For 3D QSAR Studies"; J. Med. Chem.; vol. 44, No. 15 (2001) pp. 2411–2420, 2413, 2414 Table 1.

*2* Ueda, N., Endocannabinoid hydrolases. Prostaglandins & Other Lipid Mediators 2002;68–69:521–534 (abstract only).

*2* Vogel Z., Barg J., Levy R., Saya D., Heldman E., Mechoulam R.; "Anandamide, a brain endogenous compound, interacts specifically with cannabinoid receptors and inhibits adenylate cyclase"; J. Neurochem.; 61(1) 352–355; (1993) (abstract only).

*2* Wagner JA, Varga K, Jarai Z, Kunos G; "Mesenteric Vasodilation Mediated by Endothelia Anandamide Receptors"; Hypertension (1999) 33:429–434.

PYRAZOLE DERIVATIVES AS CANNABINOID RECEPTOR ANTAGONISTS

This application is the National Stage of International Application No. PCT/US00/41239, filed Oct. 18, 2000, which claims the benefit of U.S. Provisional Application No. 60/159,993, filed Oct. 18, 1999.

FIELD OF THE INVENTION

The present invention relates generally to pyrazole derivatives and is more particularly concerned with new and improved pyrazole derivatives exhibiting high binding affinities for cannabinoid receptors, pharmaceutical preparations employing these analogs and methods of administering therapeutically effective amounts of the preparations to provide a physiological effect.

BACKGROUND OF THE INVENTION

Classical cannabinoids such as the marijuana derived cannabinoid $\Delta^9$-tetrahydrocannabinol ($\Delta^9$-THC), as well as endogenous ligands (anandamide) produce their pharmacological effects via their agonist properties at specific cannabinoid receptors in the body. So far, two cannabinoid receptors have been characterized: CB1, a central receptor found in the mammalian brain and peripheral tissues and CB2, a peripheral receptor found only in the peripheral tissues. Compounds that are agonists or antagonists for one or both of these receptors have been shown to provide a variety of pharmacological effects. See, for example, Pertwee, R.G., *Pharmacology of cannabinoid CB1 and CB2 receptors*, Pharmacol. Ther., (1997) 74:129–180 and Di Marzo, V., Melck, D., Bisogno, T., DePetrocellis, L., *Endocannabinoids: endogenous cannabinoid receptor ligands with neuromodulatory action*, Trends Neurosci. (1998) 21:521–528.

Over the last few years, a number of potent synthetic cannabinoid agonists have been developed. These agonist materials have helped in the characterization of cannabinoid receptors and with studies of receptor molecular properties.

Cannabinoid antagonists are compounds that bind to one of the CB1 or CB2 receptors but have no effect. There is considerable interest in developing cannabinoid antagonists possessing high affinity for one of the CB1 or CB2 receptors. Such cannabinoid antagonist materials provide a tool to better understand the mechanisms by which cannabinoid agonists produce their pharmacological effects and for the development of new therapeutic agents.

One class of cannabimimetic antagonists encompasses pyrazole derivatives. Pyrazole analogs have been found to act as antagonists for the CB1 and CB2 receptors, and occasionally to act as agonists for the CB1 and CB2 receptors. Most of the known materials show high receptor affinity for only the CB1 cannabinoid receptor. See for instance, Barth, F. et al, *Pyrazole Derivatives, Method Of Preparing Them And Pharmaceutical Compositions In Which They Are Present*; U.S. Pat. No. 5,624,941 to Barth et al, issued Apr. 29, 1997; Rinaldi-Carmona, M. et al, *SR141716A, A Potent And Selective Antagonist Of The Brain Cannabinoid Receptor*, FEBS Lett. 1994, 350, 240–244; Rinaldi-Carmona, M. et al, *Biochemical And Pharmacological Characterization Of SR141716A, The First Potent And Selective Brain Cannabinoid Receptor Antagonist*, Life Sci. 1995, 56, 1941–1947; and Makriyannis, A., *Structure-Activity Relationships Of Pyrazole Derivatives As Cannabinoid Receptor Antagonists*, J. Med. Chem. 42, 769–776, 1999.

SUMMARY OF THE INVENTION

The invention includes several novel pyrazole derivatives and physiologically acceptable salts thereof. The invention includes materials selective for either the CB1 or CB2 receptors. Further, some of the analogs have agonistic or antagonistic properties. Pyrazole can be represented by the formula:

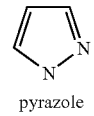

pyrazole

In one aspect of the invention, modifications were made to the pyrazole structure in the 1, 3, 4 and 5 position of the pyrazole ring. The novel pyrazole derivatives can generally be shown by structural formula 1.

structural formula 1

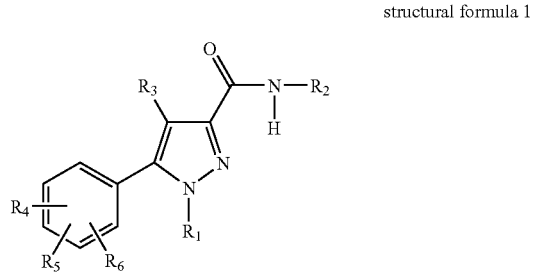

In formula 1, $R_1$ is a branched or unbranched alkyl chain having the structure $(CH_2)_nZ$ where n is an integer from 1 to about 10 and Z is selected from H, halogen, $N_3$, NCS (isothiocyanate), CN, OH, $OCH_3$, $NH_2$ and $CH=CH_2$.

$R_3$ is selected from H or a branched or unbranched chain having the structure $(CH_2)_nCH_3$ where n is an integer from 0 to about 3.

$R_4$, $R_5$ and $R_6$ are each independently selected from halogen, $N_3$, NCS, $OCH_3$, $CH_3$, $CH_2CH_3$, $NO_2$, $NH_2$, phenyl or phenyl with at least one substituent selected from halogen, $N_3$, NCS, $OCH_3$, $CH_3$, $CH_2CH_3$, $NO_2$, and $NH_2$.

$R_2$ comprises 1 or 2 linked napthyl,

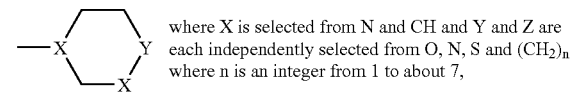 where X is selected from N and CH and Y and Z are each independently selected from O, N, S and $(CH_2)_n$ where n is an integer from 1 to about 7,

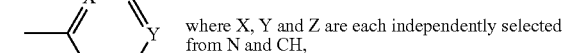 where X, Y and Z are each independently selected from N and CH,

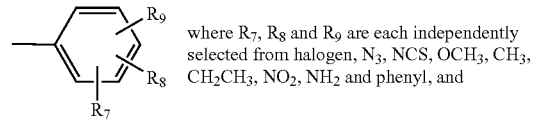 where $R_7$, $R_8$ and $R_9$ are each independently selected from halogen, $N_3$, NCS, $OCH_3$, $CH_3$, $CH_2CH_3$, $NO_2$, $NH_2$ and phenyl, and

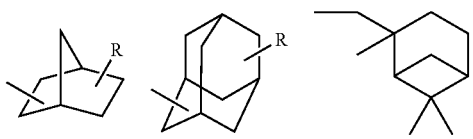

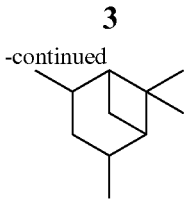

where R is selected from H, halogen, $N_3$, NCS, CN, OH, $OCH_3$, $NH_2$ and $CH=CH_2$.

The novel pyrazole derivatives surprisingly show high binding affinities for either or both of the CB1 and CB2 cannabinoid receptors. Some of the novel pyrazole analogs are cannabinoid receptor antagonists that prevent binding of endogenous agonists to the cannabinoid receptors and thereby block the biological actions of such endogenous agonists. Other novel analogs are cannabinoid receptor agonists. Therefore, the inventive analogs described herein, and physiologically acceptable salts thereof, have high potential when administered in therapeutically effective amounts for providing a physiological effect useful to treat pain, peripheral pain, glaucoma, epilepsy, nausea such as associated with cancer chemotherapy, AIDS Wasting Syndrome, cancer, neurodegenerative diseases including Multiple Sclerosis, Parkinson's Disease, Huntington's Chorea and Alzheimer's Disease, mental disorders such as Schizophrenia and depression; to suppress appetite; to reduce fertility; to prevent or reduce diseases associated with motor function such as Tourette's syndrome; to prevent or reduce inflammation; to provide neuroprotection; to modulate the immune system; to produce vasoconstriction or vasodilation and to effect memory enhancement. Thus, another aspect of the invention is the administration of a therapeutically effective amount of an inventive compound, or a physiologically acceptable salt thereof, to an individual or animal to provide a physiological effect.

Additionally, some of the novel pyrazole derivatives have functional moieties such as halogen, azide and isothiocyanate and are potentially useful diagnostic agents in vivo (PET, SPECT). Other novel pyrazole derivatives are radioligands that are potentially useful experimental tools for cannabinoid receptor studies.

DESCRIPTION OF SOME PREFERRED EMBODIMENTS

As used herein a "therapeutically effective amount" of a compound, is the quantity of a compound which, when administered to an individual or animal, results in a sufficiently high level of that compound in the individual or animal to cause a discernible increase or decrease in stimulation of cannabinoid receptors. Physiological effects that result from cannabinoid receptor stimulation include analgesia, decreased nausea resulting from chemotherapy, sedation and increased appetite. Other physiological functions include relieving intraocular pressure in glaucoma patients and suppression of the immune system. Typically, a "therapeutically effective amount" of the compound ranges from about 10 mg/day to about 1,000 mg/day.

As used herein, an "individual" refers to a human. An "animal" refers to, for example, veterinary animals, such as dogs, cats, horses and the like, and farm animals, such as cows, pigs and the like.

The compound of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to, capsular and tablet formulations (for oral and rectal administration), liquid formulations (for oral, intravenous, intramuscular, or subcutaneous administration) and slow releasing microcarriers (for rectal, intramuscular or intravenous administration). The formulations can also contain a physiologically acceptable vehicle and optional adjuvants, flavorings, colorants and preservatives. Suitable physiologically to acceptable vehicles may include, for example, saline, sterile water, Ringer's solution, and isotonic sodium chloride solutions. The specific dosage level of active ingredient will depend upon a number of factors, including, for example, biological activity of the particular preparation, age, body weight, sex and general health of the individual being treated.

The inventive pyrazole derivatives can generally be described with reference to structural Formula 1:

structural formula 1

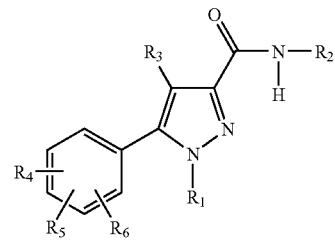

and physiologically acceptable salts thereof. With reference to structural formula 1, $R_1$ is a branched or unbranched chain having the structure $(CH_2)_nZ$ where n is an integer from 1 to about 10 and Z is selected from the group consisting of H, halogen, $N_3$, NCS, CN, OH, $OCH_3$, $NH_2$ and $CH=CH_2$.

$R_3$ is selected from the group consisting of H and a branched or unbranched chain having the structure $(CH_2)_nCH_3$ where n is an integer from 0 to about 3.

$R_4$, $R_5$ and $R_6$ are each selected from the group consisting of halogen, $N_3$, NCS, $OCH_3$, $CH_3$, $CH_2CH_3$, $NO_2$, $NH_2$, phenyl and phenyl with at least one substituent from the group consisting of halogen, $N_3$, NCS, $OCH_3$, $CH_3$, $CH_2CH_3$, $NO_2$, and $NH_2$.

$R_2$ is selected from the group consisting of napthyl,

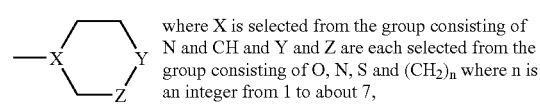
where X is selected from the group consisting of N and CH and Y and Z are each selected from the group consisting of O, N, S and $(CH_2)_n$ where n is an integer from 1 to about 7,

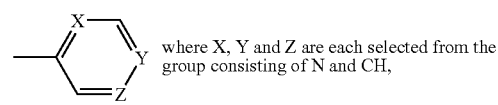
where X, Y and Z are each selected from the group consisting of N and CH,

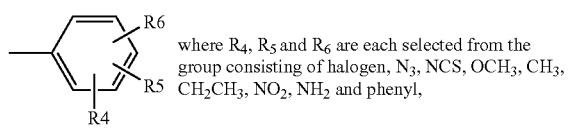
where $R_4$, $R_5$ and $R_6$ are each selected from the group consisting of halogen, $N_3$, NCS, $OCH_3$, $CH_3$, $CH_2CH_3$, $NO_2$, $NH_2$ and phenyl,

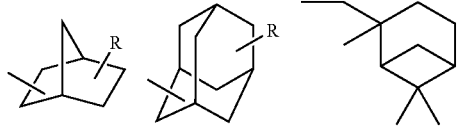

-continued

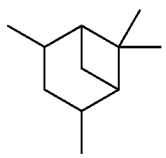

where R is selected from the group consisting of H, halogen, $N_3$, NCS, CN, OH, $OCH_3$, $NH_2$ and $CH=CH_2$.

The following examples are given for purposes of illustration only in order that the present invention may be more fully understood. These examples are not intended to limit in any way the practice of the invention. The above materials were prepared as follows. The prepared cannabimimetic pyrazole derivatives can generally be described with reference to the structures of TABLE 1 below. Naturally, the novel pyrazole derivatives are intended to include physiologically acceptable salts thereof.

TABLE 1

| Derivatives | | Ki (nM) | |
|---|---|---|---|
| | | $CB_1$ | $CB_2$ |
| 1 | | 5.98 | 2.51 |
| 2 | | 1.42 | 0.784 |
| 3 | | 14.6 | 15.4 |
| 4 | | 7.64 | 8.46 |

TABLE 1-continued

| Derivatives | | Ki (nM) | |
|---|---|---|---|
| | | CB$_1$ | CB$_2$ |
| 5 | (structure) | 19.8 | 6.65 |
| 6 | (structure) | 12.2 | 4.79 |
| 7 | (structure) | 4.73 | 2.76 |
| 8 | (structure) | 1.22 | 0.615 |
| 9 | (structure) | 1.25 | 0.682 |
| 10 | (structure) | 1.34 | 1.01 |

TABLE 1-continued

| Derivatives | Ki (nM) CB₁ | Ki (nM) CB₂ |
|---|---|---|
| 11 | 3.98 | 0.965 |
| 12 | 5.76 | 0.507 |

GENERAL

Flash column chromatography was carried out using Whatman active silica gel (230–400 mesh) and eluents were distilled before use. Solvents for reactions were dried or purified as required. Reactions were carried out under nitrogen atmospheres unless otherwise noted.

GENERAL PROCEDURE FOR THE PREPARATION OF COMPOUND 1–5 AND 7–8

Scheme 1:

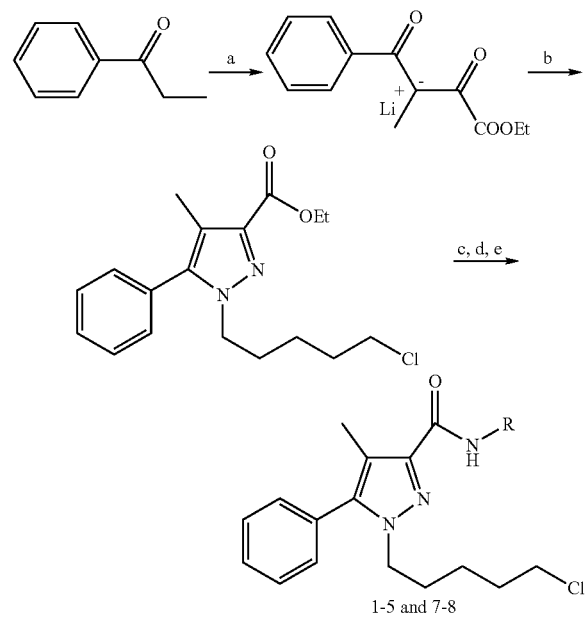

1-5 and 7-8

(a) LiHMDS, ether, then EtO₂CCO₂Et; (b) 5-Chloropentylhydrazine hydrochloride, EtOH; (c) KOH/MeOH; (d) SOCl₂, toluene; (e) Amine, Et₃N, CH₂Cl₂.

LITHIUM SALT OF ETHYL 2,4-DIOXO-3-METHYL-4-PHENYLBUTANOATE

To a magnetically stirred solution of lithium bis(trimethylsilyl)amide (40 ml, 1.0 M solution in hexane, 40 mmol) in diethyl ether (120 mL) was added a solution of propiophenone (5.37 g, 40 mmol) in diethyl ether (50 mL) at 78° C. The mixture was stirred at the same temperature for an additional 45 min, after which diethyl oxalate (6.4 mL, 47 mmol) was added to the mixture. The reaction mixture was allowed to warm to room temperature and stirred for 16 hours (h). The precipitate was filtered, washed with diethyl ether, and dried under vacuum to afford the lithium salt (7.78 g, 83% yield).

1-(5-CHLOROPENTYL)-4-METHYL-5-PHENYL-1H-PYRAZOLE-3-CARBOXYLIC ACID, ETHYL ESTER

To a magnetically stirred solution of the above lithium salt (2.0 mmol) in 10 mL of ethanol was added a solution of 5-chloropentylhydrazine hydrochloride (2.2 mmol) at room temperature. The resulting mixture was stirred at room temperature for 20 h. The solvent was removed under reduced pressure and the residue was partitioned between ethyl acetate (20 mL) and water (10 mL). The water phase was extracted with ethyl acetate (2×, 15 mL each). The ethyl acetate solution was washed with brine, dried over anhydrous sodium sulfate, filtered, and evaporated. The crude product was purified by flash column chromatography on silica gel with a petroleum ether/ethyl acetate mixture to afford the ester as a colorless oil.

COMPOUNDS 1–5 AND 7–8.

To a magnetically stirred solution of the above ethyl ester (3.4 mmol) in methanol (15 mL) was added a solution of potassium hydroxide (8.6 mmol) in methanol (12 mL). The mixture was heated under reflux for 3 hours. The cooling reaction mixture was then poured into 10 mL of water and acidified with 10% hydrochloric acid. The precipitate was filtered, washed with water, and dried under vacuum to yield the corresponding acid (1.4 g, 100% yield) as a white solid.

A solution of the crude acid (3.4 mmol) and thionyl chloride (10.3 mmol) in toluene (15 mL) was refluxed for 3 hours. The solvent was evaporated under reduced pressure. The residue was then redissolved in 40 ml of toluene and evaporated to yield the crude carboxylic chloride as an oil.

A solution of the carboxylic chloride (31.5 mmol) in dichloromethane (160 mL) was added dropwise to a solution of an appropriate amine (47.2 mmol) and triethylamine (6.5 mL, 46.7 mmol) in dichloromethane (90 mL) at 0° C. After stirring at room temperature for 3 h, brine was added to the reaction mixture, which was extracted with dichloromethane (3×, 200 mL each). The combined extracts were washed with brine, dried over anhydrous sodium sulfate, filtered, and evaporated. Flash column chromatography on silica gel with a petroleum ether/acetone (4:1) mixture gave carboxamide 1–5 and 7–8.

Scheme 2:

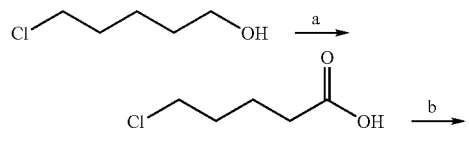

Scheme 3:

(a) PCC, CH$_2$Cl$_2$; (b) t-Butyl carbazate, hexane; (c) BH$_3$/THF; (d) 6N HCl.

5-CHLOROPENTYLHYDRAZINE HYDROCHLORIDE

A hexane solution of 5-chloropentylaldehyde (10.0 mmol) and tert-butyl carbazate (1.32 g, 10.0 mmol) was refluxed for 20 min. After cooling to the room temperature, the crystallized tert-butyl carbazate derivative was collected by filtration and dried in vacuum. A 1.0 M solution of borane tetrahydrofuran complex in tetrahydrofuran (10.0 mL, 10.0 mmol) was added to the solid tert-butyl carbazate derivative (10.0 mmol), the resulting mixture was allowed to stir at room temperature for 10 min, and then 6 N hydrochloric acid (5.0 mL) was added dropwise. The reaction mixture was refluxed for 10 min and evaporated to dryness under reduced pressure. Tetrahydrofuran was added to the residue, after which boric acid was removed by filtration. After removal of the solvent under reduced pressure, the residue was crystallized from a solution of tetrahydrofuran and diethyl ether to give 5-chloropentylhydrazine as its hydrochloride salt (71% yield).

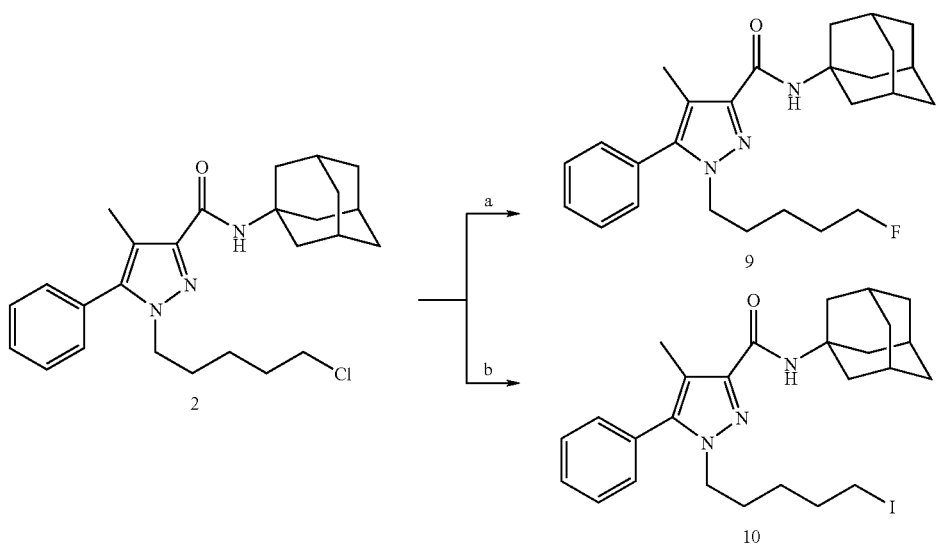

(a) TBAF, CH$_3$CN, reflux; (b) KI, acetone.

PREPARATION OF COMPOUND 9

To a magnetically stirred solution of compound 2 (0.40 g, 0.91 mmol) in acetonitrile (15 mL) was added a 1.0 M solution of tetrabutylammonium fluoride (4.5 mL, 4.5 mmol) in tetrahydrofuran and the mixture was refluxed overnight. The reaction mixture was then quenched by saturated aqueous ammonium chloride and extracted with diethyl ether (3×, 50 mL each). The combined extracts were washed with brine, dried over anhydrous sodium sulfate, filtered and evaporated. Purification by flash column chromatography on silica gel with a petroleum ether/acetone (9:1) mixture gave compound 9 as a white solid (0.296 g, 77% yield).

PREPARATION OF COMPOUND 10

To a magnetically stirred solution of compound 2 (1.12 g, 2.6 mmol) in acetone (25 mL) was added sodium iodide (1.72 g, 11.5 mmol). The reaction mixture was refluxed for 25 hours and evaporated to dryness under reduced pressure. The residue was partitioned between diethyl ether (100 mL) and water (40 mL), and the water phase was extracted with diethyl ether (3×, 30 mL each). The combined extracts were washed with brine, dried over anhydrous sodium sulfate, filtered, and evaporated. Purification by flash column chromatography on silica gel with a methylene chloride/acetone (30:1) mixture gave compound 10 as a white solid (1.27 g, 94% yield).

Scheme 4:

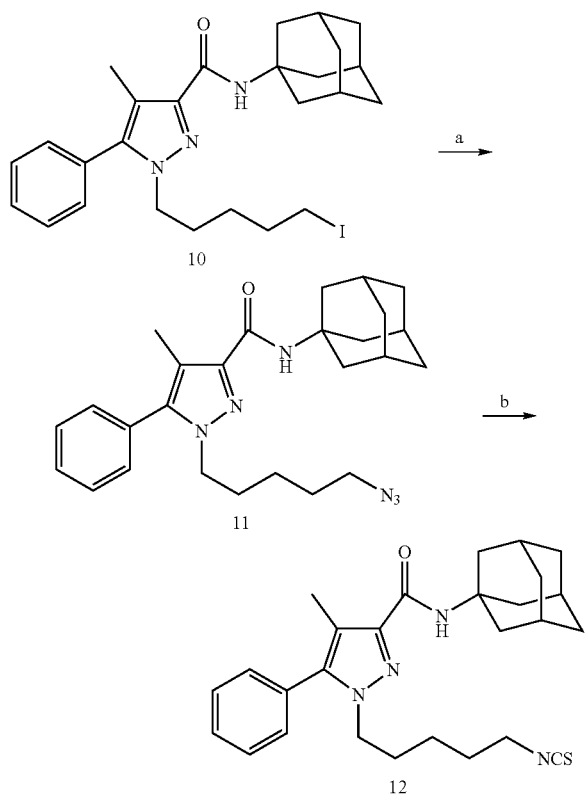

(a) NaN₃, DMF; (b) CS₂, Ph₃P, THF.

PREPARATION OF COMPOUND 11

To a magnetically stirred solution of compound 10 (0.675 g, 1.3 mmol) in anhydrous N,N-dimethylformamide (17 mL) was added sodium azide (0.83 g, 12.7 mmol). The resulting mixture was stirred at room temperature for 40 hours. Brine was then added and the reaction mixture was extracted with diethyl ether (3×, 20 mL each). The combined extracts were washed with brine, dried over anhydrous sodium sulfate, filtered and evaporated. The residue was purified by flash column chromatography on silica gel with a methylene dichloride/acetone (50:1) mixture to afford compound 11 as a white solid (0.203 g. 35.8 % yield).

PREPARATION OF COMPOUND 12

To a magnetically stirred solution of compound 11 (0.359 g, 0.8 mmol) in tetrahydrofuran (5 mL) was added triphenylphosphine (0.32 g, 1.22 mmol), followed by carbon disulfide (1.44 mL, 24 mmol). The reaction mixture was stirred at room temperature for 70 hours and then evaporated under reduced pressure. The residue was purified by flash column chromatography on silica gel with methylene dichloride to afford compound 12 (0.288 g, 77.6% yield).

PREPARATION OF COMPOUND 6

Scheme 5:

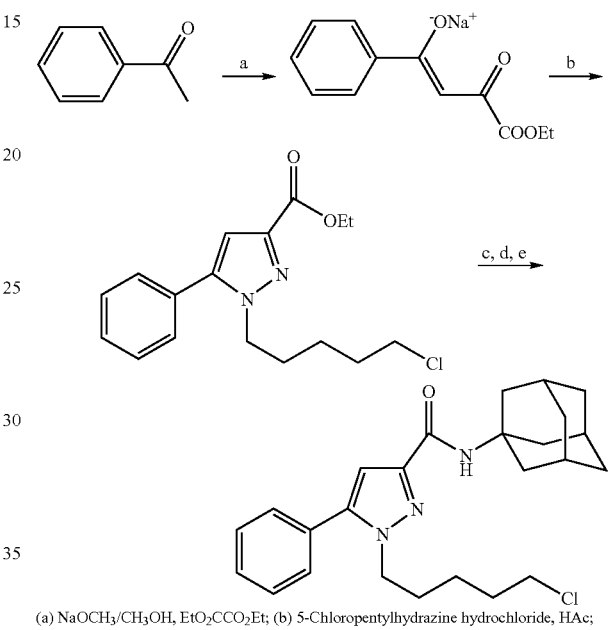

(a) NaOCH₃/CH₃OH, EtO₂CCO₂Et; (b) 5-Chloropentylhydrazine hydrochloride, HAc; (c) KOH/MeOH; (d) SOCl₂, toluene; (e) Amine, Et₃N, CH₂Cl₂.

SODIUM SALT OF METHYL BENZOYLPYRUVATE 1.3 g of sodium was dissolved in 25 mL of anhydrous methanol. A mixture of 5.8 mL of acetophenone and 6.7 mL of diethyl oxalate in 60 mL of methanol was then added, the temperature being kept below 10° C. The reaction mixture was then stirred at room temperature for 3 hours, after which 100 mL of dry ether was added. Stirring was continued for 20 min, the mixture was filtered and precipitate was washed with ether and dried under vacuum to give 6.32 g of the expected sodium salt.

1-(5-CHLOROPENTYL)-5-1H-PYRAZOLE-3-CARBOXYLIC ACID, METHYL ESTER

A suspension of 0.605 g of the sodium salt obtained above and 0.502 g of 5-chloropentylhydrazine hydrochloride in 6.5 mL of acetic acid was refluxed for 4 hours. After cooling, the mixture was poured on to 6.5 g of ice and the crystals obtained were filtered off, washed with water and dried under vacuum to give 0.42 g of ester.

COMPOUND 6

Compound 6 was prepared from the methyl ester according to the procedure described for the compound 1–5 and 7–8.

The materials were tested for CB2 receptor binding affinity and for CB1 receptor affinity (to determine selectivity for the CB2 receptor). As used herein, "binding affinity" is represented by the $IC_{50}$ value which is the concentration of an analog required to occupy 50% of the total number (Bmax) of the receptors. The lower the $IC_{50}$ value, the higher the binding affinity. As used herein an analog is said to have "binding selectivity" if it has higher binding affinity for one receptor compared to the other receptor; e.g. a cannabinoid analog which has an $IC_{50}$ of 0.1 nM for CB1 and 10 nM for CB2, is 100 times more selective for the CB1 receptor. The binding affinities ($K_i$) are expressed in nanomoles (nM) and are listed in TABLE 1.

For the CB1 receptor binding studies, membranes were prepared from rat forebrain membranes according to the procedure of P. R. Dodd et al, *A Rapid Method for Preparing Synaptosomes: Comparison with Alternative Procedures*, Brain Res., 107–118 (1981). The binding of the novel analogues to the CB1 cannabinoid receptor was assessed as described in W. A. Devane et al, *Determination and Characterization of a Cannabinoid Receptor in a Rat Brain*, Mol. Pharmacol., 34, 605–613 (1988) and A. Charalambous et al, *5'-azido $\Delta^8$ THC: A Novel Photoaffinity Label for the Cannabinoid Receptor*, J. Med. Chem., 35, 3076–3079 (1992) with the following changes. The above articles are incorporated by reference herein.

Membranes, previously frozen at −80° C., were thawed on ice. To the stirred suspension was added three volumes of TME (25 mM Tris-HCl buffer, 5 mM $MgCl_2$ and 1 mM EDTA) at pH 7.4. The suspension was incubated at 4° C. for 30 min. At the end of the incubation, the membranes were pelleted and washed three times with TME.

The treated membranes were subsequently used in the binding assay described below. Approximately 30 μg of membranes were incubated in silanized 96-well microtiter plate with TME containing 0.1% essentially fatty acid-free bovine serum albumin (BSA), 0.8 nM [$^3$H] CP-55,940, and various concentrations of test materials at 30° C. for 1 hour. The samples were filtered using Packard Filtermate 196 and Whatman GF/C filterplates and washed with wash buffer (TME containing 0.5% BSA). Radioactivity was detected using MicroScint 20 scintillation cocktail added directly to the dried filterplates, and the filterplates were counted using a Packard Instruments Top-Count. Nonspecific binding was assessed using 100 nM CP-55,940. Data collected from three independent experiments performed with duplicate determinations was normalized between 100% and 0% specific binding for [$^3$H] CP-55,940, determined using buffer and 100 nM CP-55,940. The normalized data was analyzed using a 4-parameter nonlinear logistic equation to yield $IC_{50}$ values. Data from at least two independent experiments performed in duplicate was used to calculate $IC_{50}$ values which were converted to $K_i$ values using the assumptions of Cheng et al, *Relationship Between the Inhibition Constant ($K_i$) and the concentration of inhibitor which causes 50% Inhibition ($IC_{50}$) of an Enzymatic Reaction*, Biochem. Pharmacol., 22, 3099–3102, (1973), which is incorporated by reference herein.

For the CB2 receptor binding studies, membranes were prepared from frozen mouse spleen essentially according to the procedure of P.R. Dodd et al, *A Rapid Method for Preparing Synaptosomes: Comparison with Alternative Procedures*, Brain Res., 226, 107–118 (1981) which is incorporated by reference herein. Silanized centrifuge tubes were used throughout to minimize receptor loss due to adsorption. The CB2 binding assay was conducted in the same manner as for the CB1 binding assay. The binding affinities ($K_i$) were also expressed in nanomoles (nM).

Compound SR141716A, a known pyrazole derivative, has a cannabinoid receptor affinity ($K_i$) of 11.5 nM for the CB1 receptor and 1640 nM for the CB2 receptor. As can be seen from the results in TABLE 1, all of the inventive compounds have receptor affinities much higher than compound SR141716A for at least one of the CB1 or CB2 receptors. In fact, most of the inventive pyrazole derivatives have receptor affinities much higher (lower numerically) than compound SR141716A for both of the CB1 and CB2 receptors.

The physiological and therapeutic advantages of the inventive materials can be seen from the above disclosure and also with additional reference to the following references, the disclosures of which are hereby incorporated by reference. Arnone M., Maruani J., Chaperon P, et al, *Selective inhibition of sucrose and ethanol intake by SR141716, an antagonist of central cannabinoid (CB1) receptors*, Psychopharmacal, (1997) 132, 104–106. Colombo G. Agabio R, Diaz G. et al: *Appetite suppression and weight loss after the cannabinoid antagonist SR141716*. Life Sci. (1998) 63-PL13-PL117. Simiand J, Keane M, Keane P E, Soubrie P: *SR 141716, A CB1 cannabinoid receptor antagonist, selectively reduces sweet food intake in marmoset*. Behav. Pharmacol (1998) 9:179–181. Brotchie J M: *Adjuncts to dopamine replacement a pragmatic approach to reducing the problem of dyskinesia in Parkinson's disease*. Mov. Disord. (1998) 13:871–876. Terranova J-P, Storme J-J Lafon N et al: *Improvement of memory in rodents by the selective CB1 cannabinoid receptor antagonist*, SR 141716. Psycho-pharmacol (1996) 126:165–172. Hampson A L Grimaldi M. Axpirod J. Wink D: *Cannabidiol and (−) $\Delta^9$ tetrahydrocannabinol are neuroprotective antioxidants*. Proc. Natl Acad Sci. USA (1998) 9S:8268–8273.

Buckley N E, McCoy K I, Mpzey E et al *Immunomodulation by cannabinoids is absent in mice deficient for the cannabinoid $CB_2$ receptor*. Eur. J Pharmacol (2000) 396:141–149. Morgan Dr: *Therapeutic Uses of Cannabis*. Harwood Academic Publishers, Amsterdam. (1997). Joy J E, Wagtson S J, Benson J A: *Marijuana and Medicine Assessing the Science Base*. National Academy Press, Washington, DC, USA (1999). Shen M. Thayer SA: *Cannabinoid receptor agonists protect cultured rat hippocampal neurons from excitotoxicity*. Mol. Pharmacol (1996) 54:459–462. DePetrocellis L, Melck D, Palmisano A. et al: *The endogenous cannabinoid anandamide inhibits human breaast cancer cell proliferation*. Proc Natl. Acad. Sci USA (1998) 95:8375–8380. Green K. *Marijuana smoking vs. cannabinoids for glaucoma therapy*. Arch. Ophibalmol. (1998) feb 433–1437. Hemming M, Yellowlees P M, *Effective treatment of Tourette's syndrome with marijuana*. J. Psychopharmacol, (1993) 7:389–391. Muller-Vahl K B, Schneider U, Kolbe H, Emrich, H M. *Treatment of Tourette's syndrome with delta-9-tetrahydrocannabinol*. Am. J. Psychiat. (1999) 156–195.

Muller-Vahl K B, Kolbe H, Schneider U, Emrich, H M *Cannabis in movement disorders*. Porsch. Kompicmentarmed (1999) 6 (suppl. 3) 23–27. Consroe P, Musty R, Rein J, Tillery W, Pertwee R. *The perceived effects of smoked cannabis on patents with multiple sclerosis*, Eur. Neurol. (1997) 38–44-48. Pinnegan-Ling D, Musty R. *Marinol and phantom limb pain: a case study*. Proc Inv. Cannabinoid Rea. Sec. (1994):53. Brenneisen R, Pgli A, Elsohly M A, Henn V. Spies Y: *The effect of orally and rectally administered $\Delta^9$-tetrahydrocannabinol on spasticity, a pilot study with 2 patients*. Int. J. Clin Pharmacol Ther. (1996) 34:446–452. Martyn C N. Illis L S, Thom J. *Nabilone in the* treatment of multiple sclerosis. Lancet (1995) 345:579. Maurer M, Henn V, Dittrich A, Hofmann A. *Delta-9-tetrahydrocannabinol shows antispastic and analgesic effects in a single case double-blind trial.* Eur. Arch. Psychiat. Clin. Neurosci. (1990), Z40:1–4. Herzberg U, Eliav E, Bennett G J, Kopin I J: *The analgesic effects of R(+) WIN 55,212-2 mesylate, a high affinity cannabinoid agonist in a rare model of neuropathic pain.* Neurosci. Letts. (1997) 221:157–160. Richardson J D, Kilo S. Hargreaves K M, *Cannabinoids reduce dryperalgesia and inflammation via interaction with peripheral CB1 receptors.* Pain (1998) 75:111–119. Ricardson J D, Aanonsen I, Hargreaves K M: *Antihyperalgesic effects of a spinal cannabinoids,* Eur. J. Pharmacol. (1998) 346:145–153. Calignano A, La Rana G. Diuffrida A, Piomelli D: *Control of pain initiation by endogenous cannabinoids.* Nature (1998) 394:277–291. Wagner J A, Varga K, Jarai Z, Kunos G: *Mesenteric vasodilation mediated by endothelia anandamide receptors.* Hypertension (1999) 33:429–434. Schuel, H., Burkman, L. J., Picone, R. P., Bo, T., Makriyannis, A., *Cannabinoid receptors in human sperm.* Mol. Biol. Cell., (1997) (8), 325a.

The inventive analogs described herein, and physiologically acceptable salts thereof, have high potential when administered in therapeutically effective amounts for providing a physiological effect useful to treat pain, peripheral pain, glaucoma, epilepsy, nausea such as associated with cancer chemotherapy, AIDS Wasting Syndrome, cancer, neurodegenerative diseases including Multiple Sclerosis, Parkinson's Disease, Huntington's Chorea and Alzheimer's Disease, mental disorders such as Schizophrenia and depression; to suppress appetite; to reduce fertility; to prevent or reduce diseases associated with motor function such as Tourette's syndrome; to prevent or reduce inflammation; to provide neuroprotection; to modulate the immune system; to produce vasoconstriction or vasodilation and to effect memory enhancement. Thus, another aspect of the invention is the administration of a therapeutically effective amount of an inventive compound, or a physiologically acceptable salt thereof, to an individual or animal to provide a physiological effect.

Those skilled in the art will recognize, or be able to ascertain with no more than routine experimentation, many equivalents to the specific embodiments of the invention disclosed herein. Such equivalents are intended to be encompassed by the scope of the invention.

What is claimed is:

1. A compound of the formula

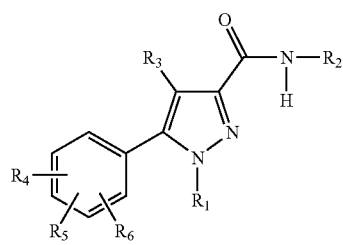

or a physiologically acceptable salt of the , wherein:

$R_1$ is a branched or unbranched alkyl chain having the structure $(CH_2)_nZ$ where n is an integer from 1 to about 10 and Z is selected from H, halogen, $N_3$, NCS, CN, OH, $OCH_3$, $NH_2$ and $CH=CH_2$;

$R_3$ is H or a branched or unbranched alkyl chain having the structure $(CH_2)_nCH_3$ where n is an integer from 0 to about 3;

$R_4$, $R_5$ and $R_6$ are each independently selected from H, halogen, $N_3$, NCS, $OCH_3$, $CH_3$, $CH_2CH_3$, $NO_2$, $NH_2$, phenyl or phenyl with at least one substituent selected from halogen, $N_3$, NCS, $OCH_3$, $CH_3$, $CH_2CH_3$, $NO_2$, and $NH_2$; and $R_2$ is selected from,

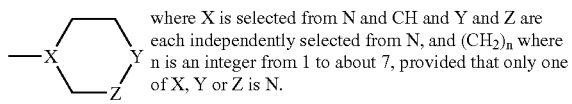 where X is selected from N and CH and Y and Z are each independently selected from N, and $(CH_2)_n$ where n is an integer from 1 to about 7, provided that only one of X, Y or Z is N.

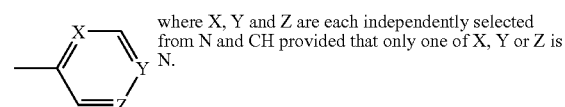 where X, Y and Z are each independently selected from N and CH provided that only one of X, Y or Z is N.

2. A method of preferentially binding to the cannabinoid receptors in an individual or animal comprising administering to the individual or animal a therapeutically effective amount of a compound having the formula

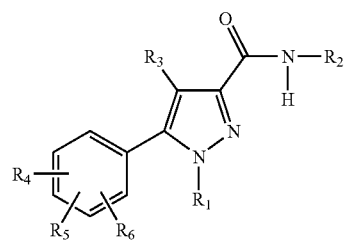

or a physiologically acceptable salt of the, wherein:

$R_1$ is a branched or unbranched alkyl chain having the structure $(CH_2)_nZ$ where n is an integer from 1 to about 10 and Z is selected from H, halogen, $N_3$, NCS, CN, OH, $OCH_3$, $NH_2$ and $CH=CH_2$;

$R_3$ is H or a branched or unbranched alkyl chain having the structure $(CH_2)_nCH_3$ where n is an integer from 0 to about 3;

$R_4$, $R_5$ and $R_6$ are each independently selected from H, halogen, $N_3$, NCS, $OCH_3$, $CH_3$, $CH_2CH_3$, $NO_2$, $NH_2$, phenyl or phenyl with at least one substituent selected from halogen, $N_3$, NCS, $OCH_3$, $CH_3$, $CH_2CH_3$, $NO_2$, and $NH_2$; and $R_2$ is selected from,

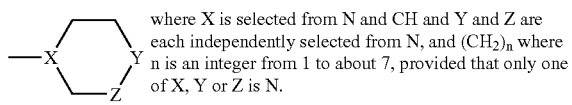 where X is selected from N and CH and Y and Z are each independently selected from N, and $(CH_2)_n$ where n is an integer from 1 to about 7, provided that only one of X, Y or Z is N.

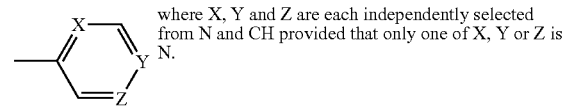 where X, Y and Z are each independently selected from N and CH provided that only one of X, Y or Z is N.

3. A pharmaceutical composition containing a therapeutically effective amount of a compound having the formula

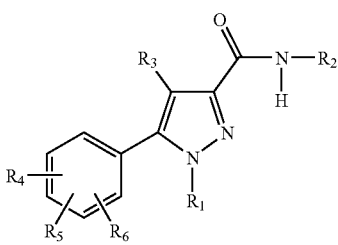

or a physiologically acceptable salt of the, wherein:
- $R_1$ comprises is a branched or unbranched alkyl chain having the structure $(CH_2)_n Z$ where n is an integer from 1 to about 10 and Z is selected from H, halogen, $N_3$, NCS, CN, OH, $OCH_3$, $NH_2$ and $CH=CH_2$;
- $R_3$ is H or a branched or unbranched alkyl chain having the structure $(CH_2)_n CH_3$ where n is an integer from 0 to about 3;
- $R_4$, $R_5$ and $R_6$ are each independently selected from H, halogen, $N_3$, NCS, $OCH_3$, $CH_3$, $CH_2CH_3$, $NO_2$, $NH_2$, phenyl or phenyl with at least one substituent selected from halogen, $N_3$, NCS, $OCH_3$, $CH_3$, $CH_2CH_3$, $NO_2$, and $NH_2$; and
- $R_2$ is selected from,

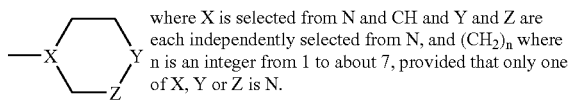 where X is selected from N and CH and Y and Z are each independently selected from N, and $(CH_2)_n$ where n is an integer from 1 to about 7, provided that only one of X, Y or Z is N.

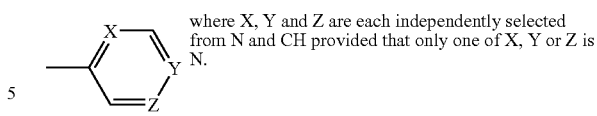 where X, Y and Z are each independently selected from N and CH provided that only one of X, Y or Z is N.

4. The compound of claim 1 wherein $R_2$ is

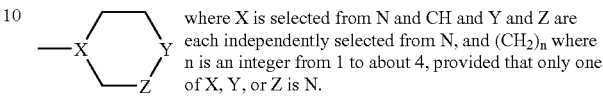 where X is selected from N and CH and Y and Z are each independently selected from N, and $(CH_2)_n$ where n is an integer from 1 to about 4, provided that only one of X, Y, or Z is N.

5. The method of claim 2 wherein $R_2$ is

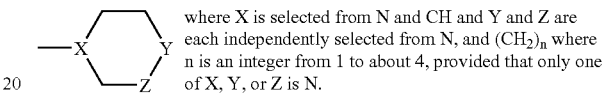 where X is selected from N and CH and Y and Z are each independently selected from N, and $(CH_2)_n$ where n is an integer from 1 to about 4, provided that only one of X, Y, or Z is N.

6. The pharmaceutical composition of claim 3 wherein $R_2$ is

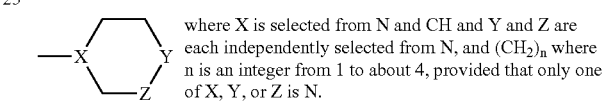 where X is selected from N and CH and Y and Z are each independently selected from N, and $(CH_2)_n$ where n is an integer from 1 to about 4, provided that only one of X, Y, or Z is N.

* * * * *

UNITED STATES PATENT AND TRADEMARK OFFICE
CERTIFICATE OF CORRECTION

PATENT NO. : 7,119,108 B1
APPLICATION NO. : 10/110865
DATED : October 10, 2006
INVENTOR(S) : Makriyannis et al.

It is certified that error appears in the above-identified patent and that said Letters Patent is hereby corrected as shown below:

Column 17:

Line 59, after "salt" delete "of the" and insert --thereof--.

Column 18:

Claim 1, Line 10, after "N" delete ",".

Claim 1, Line 12, after "N" delete "." and insert --,--.

Claim 2, Line 37, after "salt" delete "of the" and insert --thereof--.

Claim 2, Line 57, after "N" delete ",".

Claim 2, Line 59, after "N" delete "." and insert --,--.

Column 19:

Claim 3, Line 13, after "salt" delete "of the" and insert --thereof--.

Claim 3, Line 14, after "$R_1$" delete "comprises".

Claim 3, Line 29, after "N" delete ",".

Claim 3, Line 31, after "N" delete "." and insert --,--.

UNITED STATES PATENT AND TRADEMARK OFFICE
CERTIFICATE OF CORRECTION

PATENT NO. : 7,119,108 B1
APPLICATION NO. : 10/110865
DATED : October 10, 2006
INVENTOR(S) : Makriyannis et al.

It is certified that error appears in the above-identified patent and that said Letters Patent is hereby corrected as shown below:

Column 20:

Claim 4, Line 11, after "N" delete ",".

Claim 5, Line 18, after "N" delete ",".

Claim 6, Line 27, after "N" delete ",".

Signed and Sealed this

Twenty-second Day of May, 2007

JON W. DUDAS
*Director of the United States Patent and Trademark Office*